(12) United States Patent
Arumugam et al.

(10) Patent No.: US 11,984,010 B2
(45) Date of Patent: May 14, 2024

(54) SYSTEMS, APPARATUSES AND METHODS FOR ENHANCED NOTIFICATIONS TO USERS OF WEARABLE MEDICAL DEVICES

(71) Applicant: Becton, Dickinson and Company, Franklin Lakes, NJ (US)

(72) Inventors: Revathy Arumugam, Tamilnadu (IN); Ganesh Thirugnana Sambanthamoorthy, Tamilnadu (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 299 days.

(21) Appl. No.: 17/417,996

(22) PCT Filed: Dec. 20, 2019

(86) PCT No.: PCT/US2019/067880
§ 371 (c)(1),
(2) Date: Jun. 24, 2021

(87) PCT Pub. No.: WO2020/142272
PCT Pub. Date: Jul. 9, 2020

(65) Prior Publication Data
US 2022/0092960 A1 Mar. 24, 2022

Related U.S. Application Data

(60) Provisional application No. 62/786,761, filed on Dec. 31, 2018.

(51) Int. Cl.
*G08B 21/18* (2006.01)
*G08B 7/06* (2006.01)
(Continued)

(52) U.S. Cl.
CPC ............... *G08B 21/18* (2013.01); *G08B 7/06* (2013.01); *H04B 1/385* (2013.01); *H04W 4/80* (2018.02);
(Continued)

(58) Field of Classification Search
CPC .......... G08B 21/18; G08B 7/06; H04B 1/385; H04B 1/3827; H04B 1/40; H04W 4/80;
(Continued)

(56) References Cited

U.S. PATENT DOCUMENTS 9,980,140 B1 * 5/2018 Spencer ................ H04W 12/02
2007/0042769 A1 * 2/2007 Thommana ........... H04W 12/03
455/422.1
(Continued)

FOREIGN PATENT DOCUMENTS

| JP | 2018-27339 A | 2/2018 |
| WO | 2013/134279 A1 | 9/2013 |
| WO | 2015065922 A1 | 5/2015 |

OTHER PUBLICATIONS

International Search Report dated Apr. 16, 2020, which issued in counterpart PCT Patent Application No. PCT/US 19/67880.

*Primary Examiner* — James J Yang
(74) *Attorney, Agent, or Firm* — Dickinson Wright PLLC

(57) ABSTRACT

A wearable medical device (e.g., wearable drug delivery pump) sends a request to another device for generation of an audible or vibratory notification at the other device, which is helpful when the wearable medical device is obscured by a user's clothing or the user is vision or hearing impaired. The other device receiving the request to generate a notification can be a remote controller or smartphone paired with the wearable medical device, or a smart watch or a Bluetooth (BT)-enabled headset or other device paired with the remote controller. The wearable medical device is configured with a BT stack that allows the device to pair with its controller (Continued)

in a secure bonded relationship, but to send signals requiring less security (e.g., requests for generation of notifications) to other devices (e.g., a BT-enabled headset or smart watch) using a more ubiquitous wireless protocol such as a standard BT protocol with broadcast mode.

16 Claims, 12 Drawing Sheets

(51) Int. Cl.
  *H04B 1/3827* (2015.01)
  *H04W 4/80* (2018.01)
  *A61M 5/142* (2006.01)
(52) U.S. Cl.
  CPC . *A61M 5/14248* (2013.01); *A61M 2205/3584* (2013.01); *A61M 2205/581* (2013.01); *A61M 2205/582* (2013.01)
(58) Field of Classification Search
  CPC ...... A61M 5/14248; A61M 2205/3584; A61M 2205/581; A61M 2205/582; A61M 2205/502; A61M 2205/18; A61M 2205/35; A61M 2205/3576; A61M 2205/6018; A61B 5/0024; A61B 5/14532; A61B 5/4839; G06F 1/163; G06F 3/016; G06F 3/167; H04M 1/72412
  See application file for complete search history.

(56) References Cited

U.S. PATENT DOCUMENTS

| | | | |
|---|---|---|---|
| 2015/0072613 A1* | 3/2015 | Swanson | G16H 40/67 455/11.1 |
| 2015/0207915 A1* | 7/2015 | Roberts | H04L 12/1895 340/539.11 |
| 2016/0071392 A1* | 3/2016 | Hankey | A61B 5/0205 340/573.1 |
| 2016/0328529 A1 | 11/2016 | Kaib et al. | |
| 2018/0103859 A1* | 4/2018 | Provenzano | A61B 5/0024 |
| 2018/0315286 A1* | 11/2018 | Kaib | A61N 1/08 |

* cited by examiner

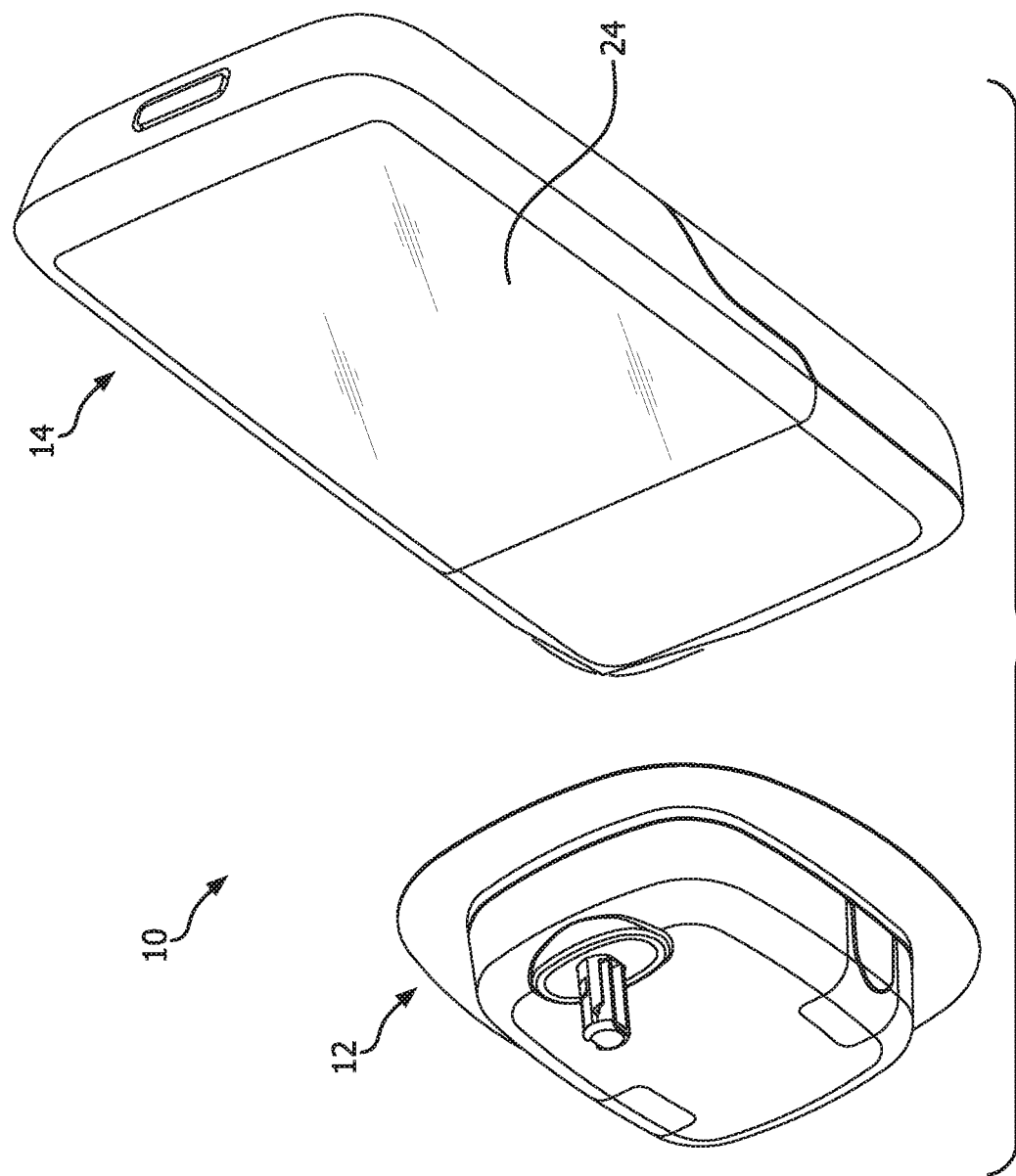

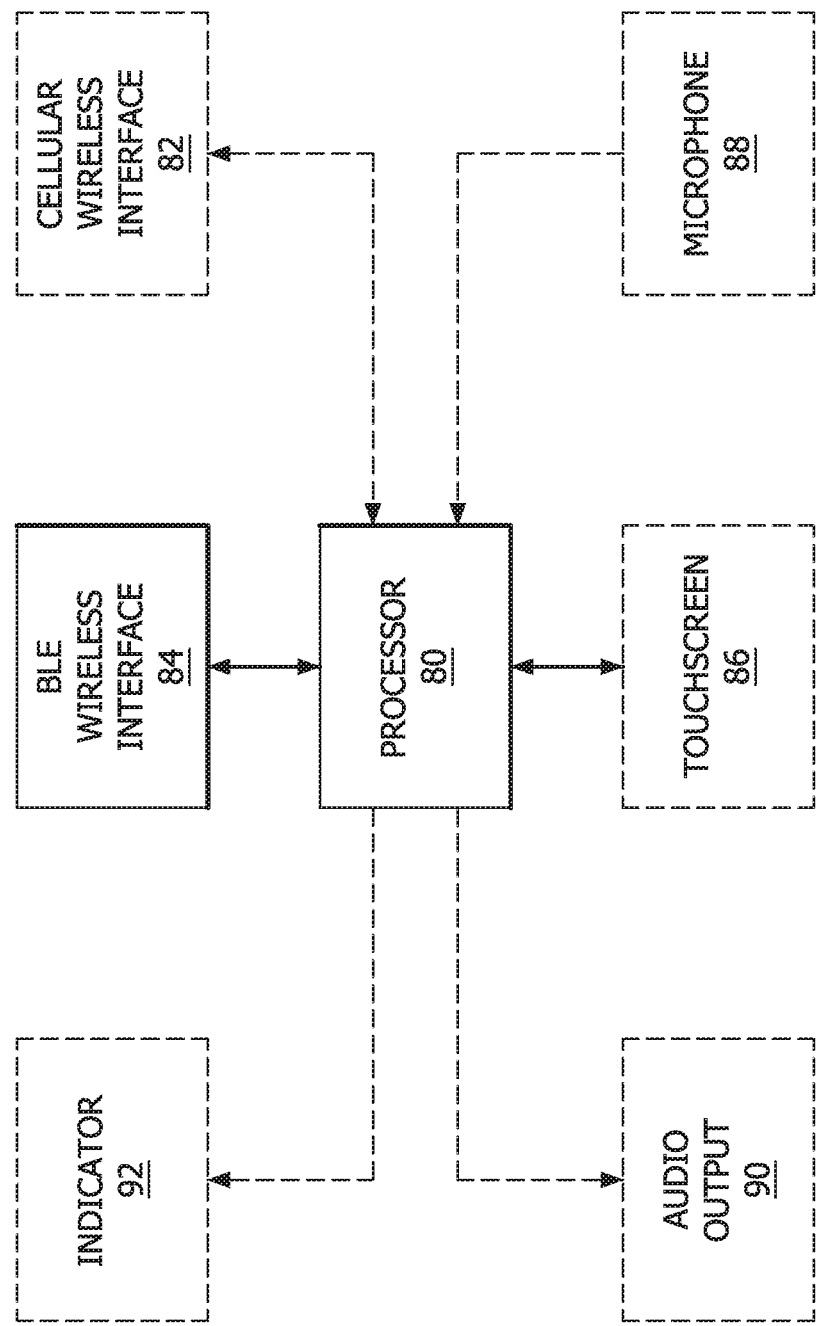

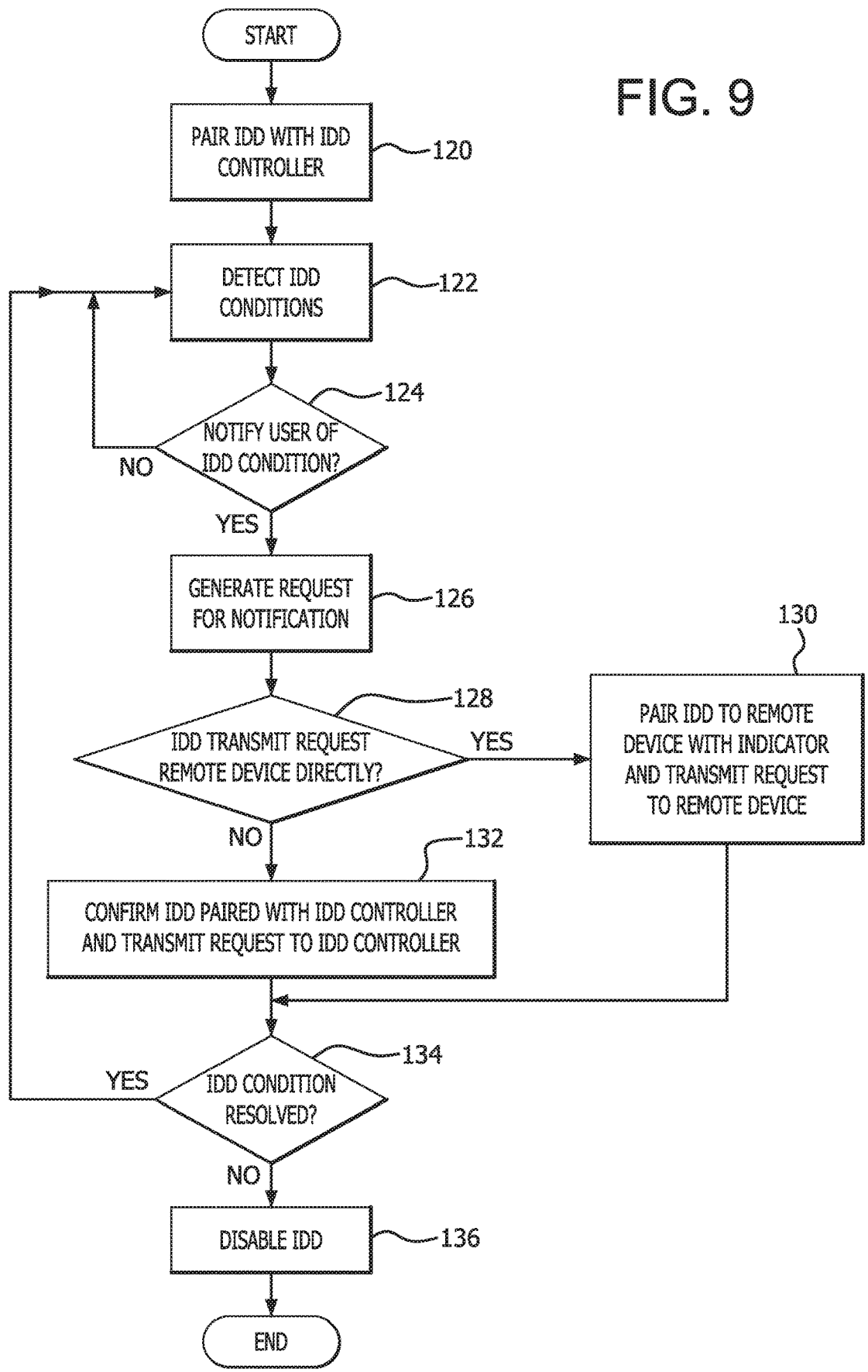

US 11,984,010 B2

SYSTEMS, APPARATUSES AND METHODS FOR ENHANCED NOTIFICATIONS TO USERS OF WEARABLE MEDICAL DEVICES

BACKGROUND

Technical Field

Example embodiments herein relate to systems, methods and apparatuses for enhanced generation of notifications to users of wearable medical devices such as fluid delivery devices.

Description of Related Art

Demand for on-body or wearable medical devices and for body area network (BAN) medical devices (e.g., wireless controllers for on-body devices, and smartphones or smart watches with a medical condition management app and/or a health/fitness app) has been increasing, along with an increase in patients' and healthcare providers' desire for better and more convenient patient management of medical conditions such as diabetes. For example, one type of wearable medical device is a wearable medication delivery device that is worn against a patient's skin (e.g., a patch pump with cannula or needle inserted into the patient's skin), or a pump device that can be connected to a patient's belt, for example, and having an infusion set with tubing extending from the pump to an adhesive mount with a subcutaneous cannula.

A wearable medical device can communicate wirelessly with a separate dedicated controller or smartphone (e.g., a smartphone with app configured to wirelessly interface with the wearable medical device for various operations). Bluetooth® Low Energy (BLE), marketed as Bluetooth® Stuart, is a wireless technology that provides an effective, low power protocol for wirelessly connecting devices, including devices that run on power sources such as coin cell batteries as can often be the case with wearable medical devices.

A concern with wirelessly controlling a wearable medical device, particularly a device that delivers medication to a patient's body, is security of the wireless control communication link against man-in-the-middle (MITM) and eavesdropping attacks. Of particular concern is security of a wearable medical device against nefarious attacks or unintentional attacks wherein control of the medical device is undesirably altered by another device.

Another concern with wearable medical devices is the ability of users to receive alerts from their device. For example, visual alerts generated on a display of a wearable medical device can be difficult for some users to see, particularly when the display is obscured by a user's clothes or the user is visually impaired.

SUMMARY OF THE INVENTION

The problems are overcome, and additional advantages are realized, by illustrative embodiments described below.

In accordance with illustrative embodiments, a wearable medical device (e.g., wearable drug delivery pump) sends a request to another device for generation of an audible or vibratory notification at the other device, which is helpful when the wearable medical device is obscured by a user's clothing or the user vision or hearing is impaired. The other device receiving the request to generate a notification can be a remote controller or smartphone paired with the wearable medical device, or a smart watch or a Bluetooth (BT)-enabled headset or other device paired with the remote controller. The wearable medical device is configured with a BT stack that allows the device to pair with its controller in a secure bonded relationship, but to send signals requiring less security (e.g., requests for generation of notifications) to other devices (e.g., a BT-enabled headset or smart watch) using a more ubiquitous wireless protocol such as a standard BT protocol with broadcast mode.

In accordance with illustrative embodiments, a medical device is provided, comprising: a radio frequency (RF) circuit configured to exchange RF signals with a second device; a memory device; and a processing device connected to the RF circuit and the memory device, and configured to detect at least one designated notification condition in the medical device, generate a request for notification in response to detection of at least one designated notification condition, and transmit via the RF circuit the request wirelessly to the second device to prompt the second device to actuate an indicator that is remote from the medical device.

In accordance with aspects of illustrative embodiments, the medical device is a wearable device. The second device is at least one device chosen from a controller and a smartphone and is paired wirelessly with the medical device, the second device having at least one indicator chosen from an audible indicator and a tactile indicator.

In accordance with aspects of illustrative embodiments, the second device is paired with a third device, and the third device comprises at least one indicator chosen from an audible indicator and a tactile indicator. For example, the third device is selected from the group consisting of a smart watch, a Bluetooth®-enabled headset, a portable monitoring device, and a Bluetooth®-enabled wristband device.

In accordance with aspects of illustrative embodiments, the processing device and RF circuit of the medical device are configured to employ a selected one of at least two wireless communication protocols to exchange, via the RF circuit, RF signals with at least one device chosen from the second device and the third device. The at least two wireless communication protocols comprise a first communication protocol that is employed by the processing device to pair the second device with the medical device to securely send secure information chosen from configuration data, medical device operation data, and control signals to operate the medical device, and a second communication protocol that is employed by the processing device to pair with at least one of the second device and the third device to send information chosen from medical device status data and notifications that requires less wireless security than the secure information.

In accordance with aspects of illustrative embodiments, the medical device further comprises a user interface. The processing device is configured to operate the user interface to generate user selection prompts that guide a user to configure notification preferences based on criteria chosen from paired device selection and corresponding notification mode, wherein the paired device selection prompts a user to indicate at least one device paired with the medical device, and wherein the notification mode prompts the user to select a mode chosen from an audible mode and a tactile mode to be employed by that paired device for the notification.

In accordance with illustrative embodiments, a device is provided for generating a notification from a medical device, comprising at least one indicator; a radio frequency (RF) circuit configured to exchange RF signals with the medical device; a memory device; and a processing device connected to the at least one indicator, the RF circuit and the memory device, and configured to wirelessly receive via the RF circuit a request for notification from the medical device, the medical device generating the request for notification in response to detection of at least one designated notification condition, and to perform a notification operation chosen from generating an audible signal via the at least one indicator, wirelessly transmitting via the RF circuit a request to a third device to generate an audible signal, generating a vibratory notification signal via the at least one indicator, and wirelessly transmitting via the RF circuit a request to the third device to generate a vibratory notification signal.

In accordance with aspects of illustrative embodiments, the device is at least one device chosen from a controller and a smartphone and is paired wirelessly with the medical device. The third device is selected from the group consisting of a smart watch, a Bluetooth®-enabled headset, a portable monitoring device, and a Bluetooth®-enabled wristband device.

In accordance with aspects of illustrative embodiments, the device further comprises a user interface. The processing device is configured to operate the user interface to generate user selection prompts that guide a user to configure notification preferences based on criteria chosen from paired device selection and corresponding notification mode, wherein the paired device selection prompts a user to indicate at least one device paired with the medical device, wherein the notification mode prompts the user to select a mode chosen from an audible mode and a tactile mode to be employed by that paired device for the notification, and wherein the paired device is chosen from the device, the third device and a fourth device.

In accordance with illustrative embodiments, a method of generating a notification from a medical device is provided that comprises: configuring the medical device to detect at least one designated notification condition; configuring the medical device to generate a request for notification in response to detection of at least one designated notification condition; transmitting the request wirelessly to a second device comprising an indicator, the second device actuating the indicator in response to the request.

In accordance with aspects of illustrative embodiments, the indicator is an audio output device configured to output an audible output signal. The second device is selected from the group consisting of a cell phone, a Bluetooth-enabled ear piece, a smart watch, a portable communication device, a portable computing device, a portable wireless controller configured to control the medical device.

In accordance with aspects of illustrative embodiments, the notification condition is selected from the group consisting of an end of life state of the medical device, a corrupted memory in the medical device, near empty reservoir in the medical device, empty reservoir in the medical device, and low battery in the medical device.

In accordance with aspects of illustrative embodiments, the method of generating a notification from a medical device further comprises generating user selection prompts that guide a user to configure notification preferences based on criteria chosen from paired device selection and corresponding notification mode, wherein the paired device selection prompts a user to indicate at least one device paired with the medical device, and wherein the notification mode prompts the user to select a mode chosen from an audible mode and a tactile mode to be employed by that paired device for the notification.

In accordance with illustrative embodiments, a method of generating a notification from a medical device comprises wirelessly receiving a request for notification from the medical device at a second device, the medical device being configured to generate the request for notification in response to detection of at least one designated notification condition; and operating the second device to perform a notification operation chosen from generating an audible signal via at least one indicator, wirelessly transmitting a request to a third device to generate an audible signal, generating a vibratory notification signal via at least one indicator, and wirelessly transmitting a request to the third device to generate a vibratory notification signal.

In accordance with aspects of illustrative embodiments, the method further comprises the third device actuating an indicator in response to receiving the request transmitted from the second device.

In accordance with aspects of illustrative embodiments, the method further comprises generating, via a device chosen from the medical device, the second device and the third device, user selection prompts that guide a user to configure notification preferences based on criteria chosen from paired device selection and corresponding notification mode, wherein the paired device selection prompts a user to indicate at least one device paired with the medical device, wherein the notification mode prompts the user to select a mode chosen from an audible mode and a tactile mode to be employed by that paired device for the notification, and wherein the paired device is chosen from the second device, the third device and a fourth device.

Additional and/or other aspects and advantages of illustrative embodiments will be set forth in the description that follows, or will be apparent from the description, or may be learned by practice of the invention. The present invention may comprise devices to be paired and methods for operating same having one or more of these aspects, and/or one or more of the features and combinations thereof. The present invention may comprise one or more of the features and/or combinations of these aspects as recited, for example, in the attached claims.

BRIEF DESCRIPTION OF THE DRAWINGS

The above and/or other aspects and advantages of example embodiments will be more readily appreciated from the following detailed description, taken in conjunction with the accompanying drawings, of which:

FIG. 1 depicts a medical device and a controller in accordance with an illustrative embodiment:

FIGS. 2A, 2B and 2C are block diagrams, respectively, of the medical device and the controller of FIG. 1 and of another device in accordance with an illustrative embodiment;

FIG. 9 is a flow chart depicting operations of the medical device to request a notification generated at another device in accordance with an illustrative embodiment.

Throughout the drawing figures, like reference numbers will be understood to refer to like elements, features and structures.

DETAILED DESCRIPTION OF ILLUSTRATIVE EMBODIMENTS

Figure 2A:
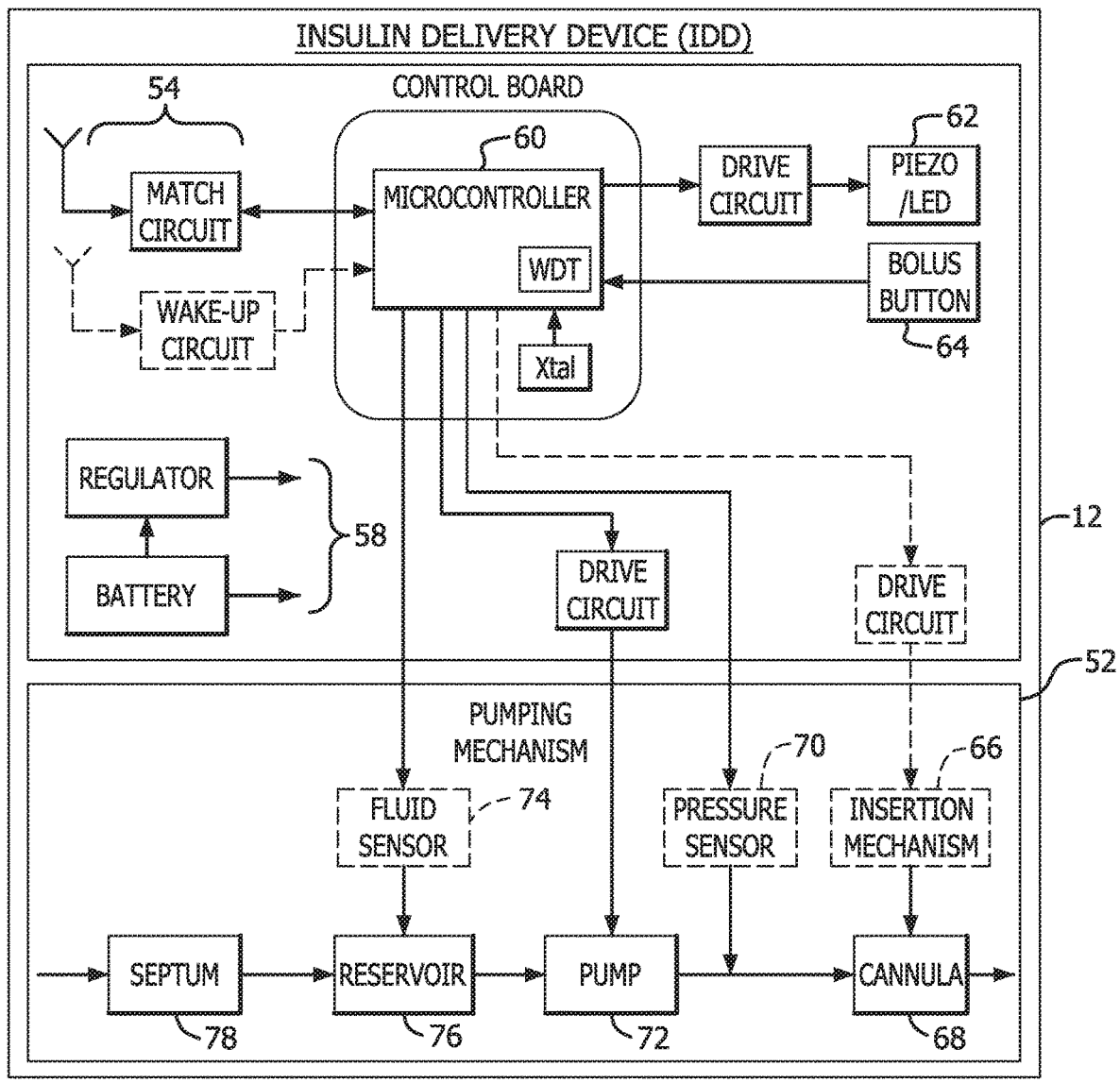

Reference will now be made in detail to example embodiments, which are illustrated in the accompanying drawings.

Problems are overcome and advantages are realized, by illustrative embodiments described below wherein a wearable medical device communicates a request for indication generation (e.g., alarms/notifications of certain wearable medical device conditions) by another wearable or portable, handheld device. The wearable medical device is configured with a Bluetooth® (BT) stack that allows the device to pair with its controller in a secure bonded relationship, but to send signals requiring less security (e.g., requests for generation of notifications) to other devices (e.g., a BT-enabled headset or smart watch) using a more ubiquitous standard BT protocol with broadcast mode. The wearable medical device communicates the request for indication generation using a standard BT protocol, which allows the wearable medical device to engage a greater variety of devices for alarm/notification generations than simply the controller to which it is paired using a proprietary BT protocol with additional security against unintended control operations of the wearable medical device by other devices.

With reference to FIG. 1, an illustrative medication delivery system 10 is shown having a wearable medical device 12, and a controller 14 with display 24 or other user interface. As will be described herein and in accordance with illustrative embodiments, the medical device 12 can be used with a dedicated controller 14 or with a smartphone with an app 14 configured to operate as a controller 14, and the medical device 12 can also be connected directly, or indirectly, via its controller 14 to other devices 16 or smartphone apps 16 that provide additional functions. These other devices 16 or smartphone apps 16 can be related, for example, to one or more BAN devices such as a blood glucose meter, smart watch, exercise monitor, Bluetooth® headset and the like. The medical device 12, the dedicated controller 14 or device control app 14 in a smartphone, and the other devices 16 or smartphone apps 16 that provide additional functions, are configured to have communication links with each other and optionally with additional devices in a LAN, WAN or internet cloud, while minimizing likelihood of MITM and eavesdropping attacks such as nefarious attacks wherein control of the medical device 12 is undesirably altered by another device. For example, as described below in connection with illustrative embodiments, the medical device 12 and the controller 14 can employ a secure, BLE-based intradevice communication protocol for secure control operations such as medication delivery, and a standard interdevice Bluetooth® protocol (e.g., legacy Classic Bluetooth®) can be used for pairing the medical device 12 with controller device 14 and/or devices 16 (e.g., Bluetooth® headsets or earpieces or smart watches) to merely generate notification or exchange information (e.g., status data or log data) but not control the medical device 12 configuration or dosing operations (e.g., not specifying or setting bolus amounts, initiating and terminating pump delivery operations, or providing sensitive device data such as delivered drug amounts).

The medical device 12 can be, for example, a disposable insulin delivery device (IDD) 12 for single patient use that is configured for continuous subcutaneous delivery of insulin at set and variable basal (24-hour period) rates and bolus (on-demand) doses for the management of patients with Type 2 Diabetes Mellitus (T2DM) requiring insulin therapy. It is to be understood, however, that the medical device 12 can be any on-body medical device (e.g., wearable infusion pump or continuous glucose meter) or BAN medical device (e.g., handheld blood glucose meter, smartphone with medical condition management apps, dedicated wireless controller for on-body device, smart watch, or wearable fitness and health monitor). It also is to be understood, however, that if the medical device 12 is a medication delivery device, it can be used to deliver any type of fluid and is not limited to insulin delivery.

The IDD 12 addresses an unmet need for many Type 2 patients on multiple daily injections (MDI) requiring a discreet, simple and cost effective insulin delivery alternative to the traditional complex insulin pump. With continued reference to FIGS. 1, 2A and 2B, the IDD 12 is part of a system 10 that is an advanced insulin delivery system for use by patients with T2DM. The IDI) 12 is configured for 24-hour-a-day use in all environments typically inhabited by the target users. The IDD 12 is configured to allow the patient user to wear the IDD for a period of three days (up to 84 hours). The IDD 12 has four (4) main functions: delivering user-set daily basal insulin rate; delivering user-set bolus insulin amount; delivering manual bolus insulin dose(s); and generating system status and notifications.

As described below, the IDD 12 communicates wirelessly with its controller (i.e., hereinafter referred to as the wireless controller (WC 14)) through a Bluetooth® Low Energy (BLE) interface. In addition to IDD operational data, the IDD 12 sends feedback to the WC 14 if it detects issues with the IDD (e.g., memory corruption, low or empty reservoir, low battery). The WC 14 is configured to program the IDD 12 to deliver a daily basal insulin rate and bolus or food dose insulin amount to the patient. The WC 14 is configured to also provide status information about the system 10. The WC 14 also enables connectivity to a BLE Wireless Connected Device Interface (BWCDI) of an external device 16 for data exchange. As such, WC 14 can send a request for generation of a notification, or optionally IDD 12 data, to an external device 16 via a BWCDI.

An important function supported by communication software in the system 10 is the wireless communication between the WC 14 and IDD 12, which enables the IDD 12 to provide the feedback to the WC 14 and for the user to control their insulin delivery by the IDD 12 wirelessly via the WC 14 in a simple and discreet way. Sometimes, when the IDD 12 feedback to the WC 14 indicates an issue with the IDD (e.g., a malfunction or problem with the IDD), a notification needs to be generated and provided to the user. A notification can be, for example, a visual alert such as a display on a graphical user interface screen, or activation of a light-emitting diode (LED), provided on the IDD 12 or the WC 14. Visual alerts, however, can be difficult for some users to see, particularly when an alert is generated at the IDD 12 and the IDD 12 is obscured by a user's clothes or the user is visually impaired.

A need therefore exists for providing enhanced notifications to a user of a wearable medical device. A number of example, enhanced notification methods and related devices are described below in accordance with illustrative embodiments. An example IDD 12 and example WC 14 are described below with reference to FIGS. 2A through 10 for illustrative purposes. It is to be understood that the enhanced notification methods in the illustrative embodiments can be used with different medical devices 12 (e.g., IDDs) and controllers or WCs 14 having different configurations, functions and operations than those shown and described with reference to FIGS. 2A through 10. As described herein, the example IDD 12 is disposable. Accordingly, a need also exists for enhanced notifications operations of an IDD 12 that does not add to the complexity and cost of the IDD.

In the illustrated embodiment shown in FIG. 2A, the IDD 12 has a microcontroller 60 configured to control a pumping mechanism 52, wireless communication with the WC (e.g., via an RF circuit 54 having a match circuit and antenna), and pump operations. The IDD has a bolus button(s) 64 for manual delivery of medication in addition to programmed delivery of medication. The pumping mechanism 52 comprises a reservoir 76 for storing a fluid medication (e.g., insulin) to be delivered via a cannula 68 to the patient wearing the IDD, and a pump 72 for controllably delivering designated amounts of medication from the reservoir through the cannula. The reservoir 76 can be filled via a septum 78 using a syringe. The IDI) has a manual insertion mechanism 66 for inserting the cannula 68 into a patient; however, the processor 60 can be configured to operate an optional drive circuit to automate operation of the insertion mechanism 66 to deploy the cannula 68 into the patient. Further, the IDD 12 can be optionally provided with a fluid sensor 74 or a pressure sensor 70 for occlusion detection, for example. An LED 62 can be operated by the microcontroller 60 to be on or flash during one or more pump operations such as during reservoir priming, for example. As stated above, the LED can be obscured by the user's clothes or otherwise disposed on the IDD to not be in view once the IDD is adhered to the user's skin. The IDD 12 is powered by a battery and regulator as indicated at 58. When initializing the IDD 12 (e.g., powering on to begin pairing with the WC 12), the bolus button(s) 64 can be configured as wake-up button(s) that, when activated by the user, causes the IDD 12 to wake from a power conserving shelf mode. In the illustrated embodiment, the IDD 12 is not provided with a user interface other than wake-up button(s) since such an addition of a touch screen or other display screen to the IDD 12 would disadvantageously increase its cost and possibly its form factor size.

Figure 2B:
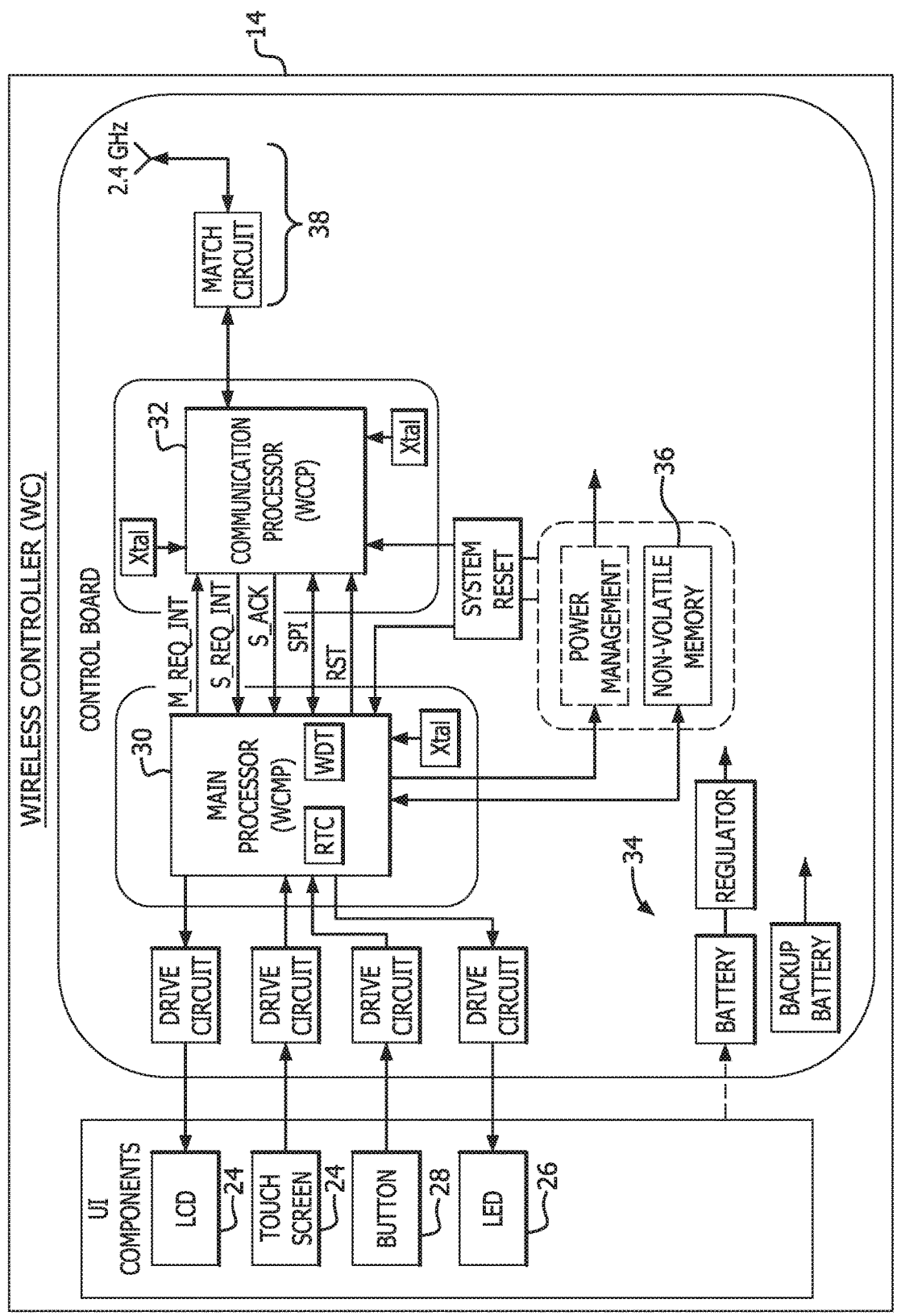

In the illustrated embodiment shown in FIG. 2B, the WC 14 can be implemented as a dual microprocessor component having: 1) a WC Main Processor (WCMP) 30, and a WC Communications Processor (WCCP) 32. It is to be understood, however, that the WC 14 can be configured as a single processor device. The two processors 30, 32 communicate with each other through a serial peripheral interface (SPI). The two processors 30, 32 can also interrupt each other through two interrupt pins, M_REQ_INT and S_REQ_INT.

With reference to FIG. 2B, the WCMP 30 is connected to the user interface (UI) components such as the LCD display with touch screen 24, one or more buttons 28, optional indicator 26 (e.g., speaker, vibration circuit, LED, buzzer), and the like. The WCCP 32 is connected to radio frequency (RF) components 38 (e.g., an antenna and a match circuit) and is mainly responsible for the WC 14's wireless communication with the IDD 12, It is to be understood, however, that the RF components 38 can comprise one or more antennas and related circuitry to communicate with other devices 16 via different communication protocols. The WC 14 is designed to be non-field serviceable (i.e. no parts to be inspected, adjusted, replaced or maintained by the user), except for replaceable alkaline batteries 34 for power. A non-volatile memory (e.g., FLASH memory) 36 is provided in the WC to store delivery and status data received from the IDD 12 such as delivery dates and times and amounts.

With continued reference to FIG. 2B, the LCD with capacitive touch screen 24 serves as the visual interface for the user by rendering visual and graphical outputs to the user (e.g., system information, instructions, visual notices, user configurations, data outputs, etc.), and by providing a visual interface for the user to enter inputs (e.g., device operation inputs such as IDD pairing and set up and dosing, and configuration parameters, and so on) The WC display with capacitive touch screen 24 detects at least single-touch gestures over its display area. For example, the touch screen is configured for recognizing user tactile inputs (tap, swipe, and button press), allowing for navigation within UT screens and applications. The touch screen 24 aids in executing specific system functionalities (i.e. IDD 12 setup and pairing with the WC 14, insulin dosing, providing user with dosing history, and IDD deactivation and replacement with another IDD, and so on) through specific user interactions. The WC 14 can also include a button 28 such as a device wake-up button that, when activated by the user, causes the WC 14 to wake from a power conserving sleep mode. The WC 14 can also have an LED 26 to indicate low battery status (e.g., indicate low battery state when there is 12 hours or less of usage remaining).

The WC 14 radio frequency (RF) interface with the IDD 12 is, for example, based on a Bluetooth® Low Energy or BLE-based communication protocol, although other wireless communication protocols can be used. In the example medication delivery system 10, the WC 14 and IDD 12 communicate wirelessly within a distance of up to 10 feet or approximately 3 meters, utilizing the ISM band from 2400 MHz to 2480 MHZ spectrum. The WC 14 communicates with the IDD 12 while the IDD is adhered to the body in open air. The WC 14 is the central device or master, and the IDD 12 is the peripheral device or slave. Whenever the WCMP 30 wants to send information to the IDD 12 or retrieve information from the IDD 12, it does so by interacting with the WCCP 32, which in turn, communicates with the IDD 12 across the BLE link via the respective RF circuits 54 and 38, as shown in FIGS. 2A and 29 respectively.

FIG. 2C is a block diagram depicting an example device 16. The device 16 can be a smartphone, smart watch, Bluetooth®-enabled health and/or fitness monitoring device, Bluetooth®-enabled headset or earpiece, among other Bluetooth®-enabled wireless devices 16, for example. The device 16 comprises a processor and memory 80 that can be integrated or separate components. The device 16 can have a Bluetooth®-enabled wireless communications interface 84 and an optional cellular communications interface 82, for example. The device 16 can also have different user interfaces such as one or more of a microphone 88, touchscreen 86 or keypad or other user input device, an audio signal output device (e.g., speaker or buzzer) 90, and/or another indicator such as a vibration circuit 92. The WC 14 communicates with the device 16 across a BLE link, for example, via respective RF circuits and BLE wireless interfaces.

In accordance with an aspect of illustrative embodiments, the WC 14 (e.g., its WCCP 32) and the IDD 12 can communicate in accordance with a specific intradevice pairing protocol and various operations to mitigate risk that the WC 14 pairs with an unintended MD 12' or, vice versa, that an intended IDD 12 pairs with an unintended WC 14' as described, for example, in commonly owned PCT published applications. WO 2018/183036 and WO 2018/183038, which are incorporated herein by reference. As defined herein, "intradevice" refers to the WC 14 being paired with and bonded with one particular medical device 12 (e.g., IDD 12). Either unintended pairing scenario could cause unintended operation or control of the pumping mechanism 52, potentially resulting in insulin over-infusion that can be injurious to the patient. In accordance with another aspect of illustrative embodiments, the WC 14 can also communicate with another device(s) 16 in accordance with a more ubiquitous interdevice communication protocol (e.g., a protocol that is more commonly used by different commercially available devices 16), to enable the WC 14 to send less sensitive data than medical device control commands to various devices 16. As defined herein, "interdevice" refers to the WC 14 being able to send selected IDD 12 information with one or more other devices 16.

For example, Bluetooth® Low Energy (BLE), marketed as Bluetooth® Smart, is a wireless technology for establishing packet-based wireless networks among wireless devices operating in the 2.4 GHz to 2.4835 GHz frequency range with significantly reduced power consumption compared to legacy Bluetooth® devices, which are sometimes referred to as Classic Bluetooth® devices. Low power wireless devices compliant with the Bluetooth® Smart specification are advantageous for healthcare applications because they are expected to run for long periods of time on a button or coin battery. Bluetooth® Smart Ready devices are wireless devices with dual protocol stacks capable of communicating with legacy Classic Bluetooth® devices, as well as Bluetooth® Smart devices. For example, a smartphone with IDD control app 16 can have Bluetooth® Smart Ready operation so that it can communicate with a legacy Classic Bluetooth® device 16 such as an activity monitor or continuous glucose monitor (CGM), as well as a personal device such as an IDD 12 having Bluetooth® Smart operation to allow for pairing using, for example, the specific intradevice pairing protocol to restrict which device 14 the IDD 12 can exchange pump operation data with and receive control commands from.

Figure 3:
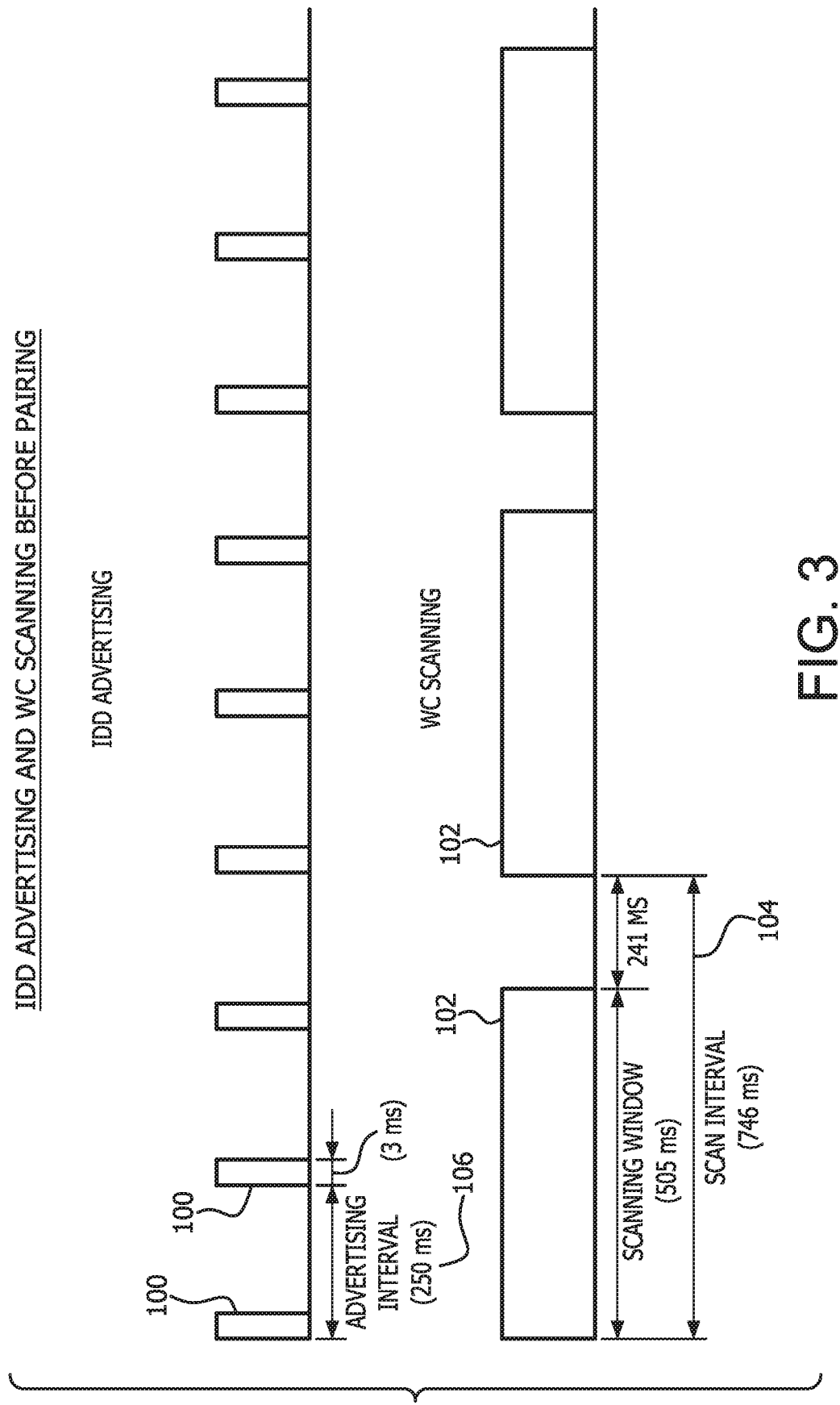
FIGS. 3, 4 and 5 are diagrams of signals transmitted from the medical device and the controller in accordance with an illustrative embodiment.
Figure 4:
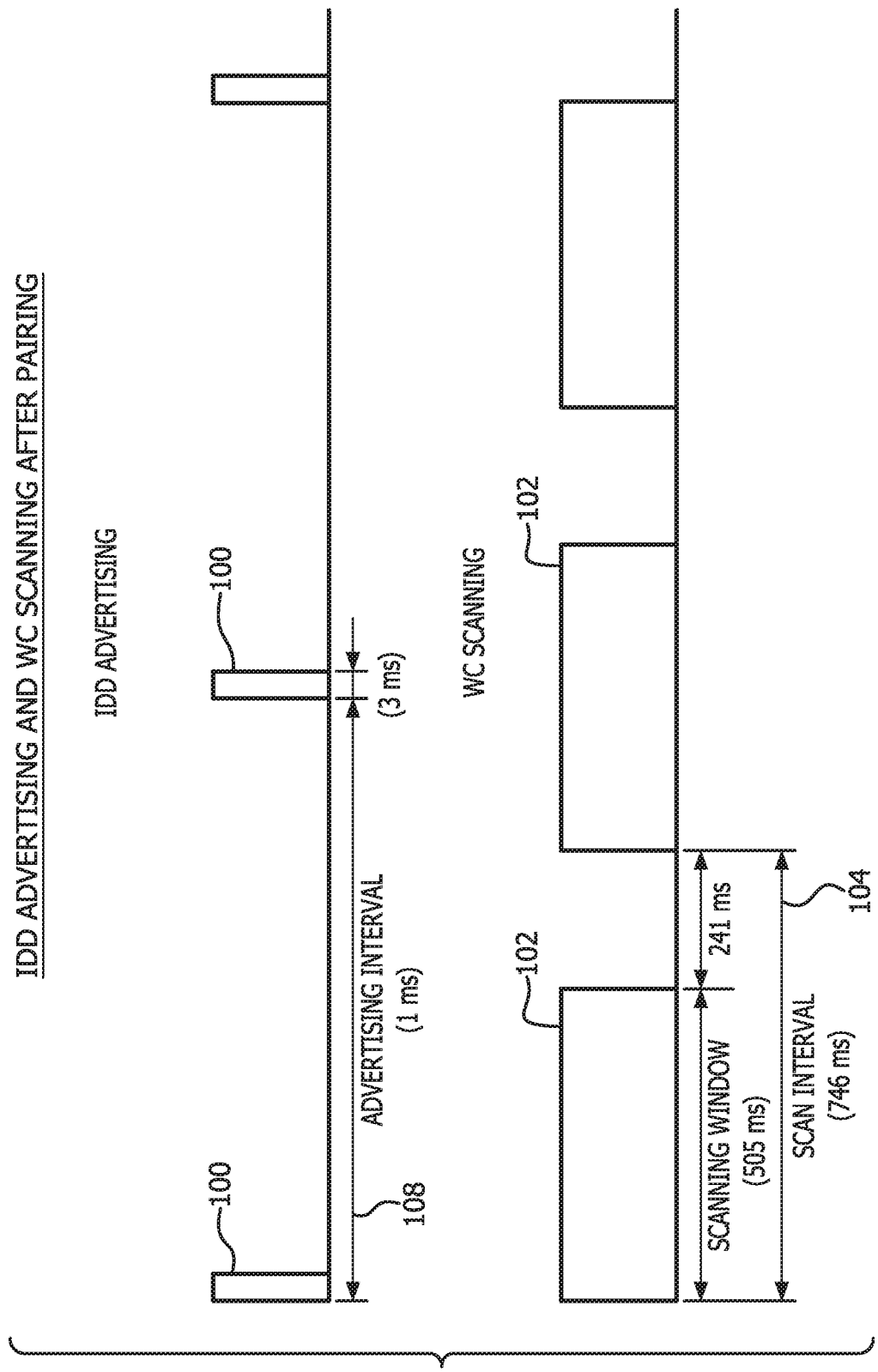
Figure 5:
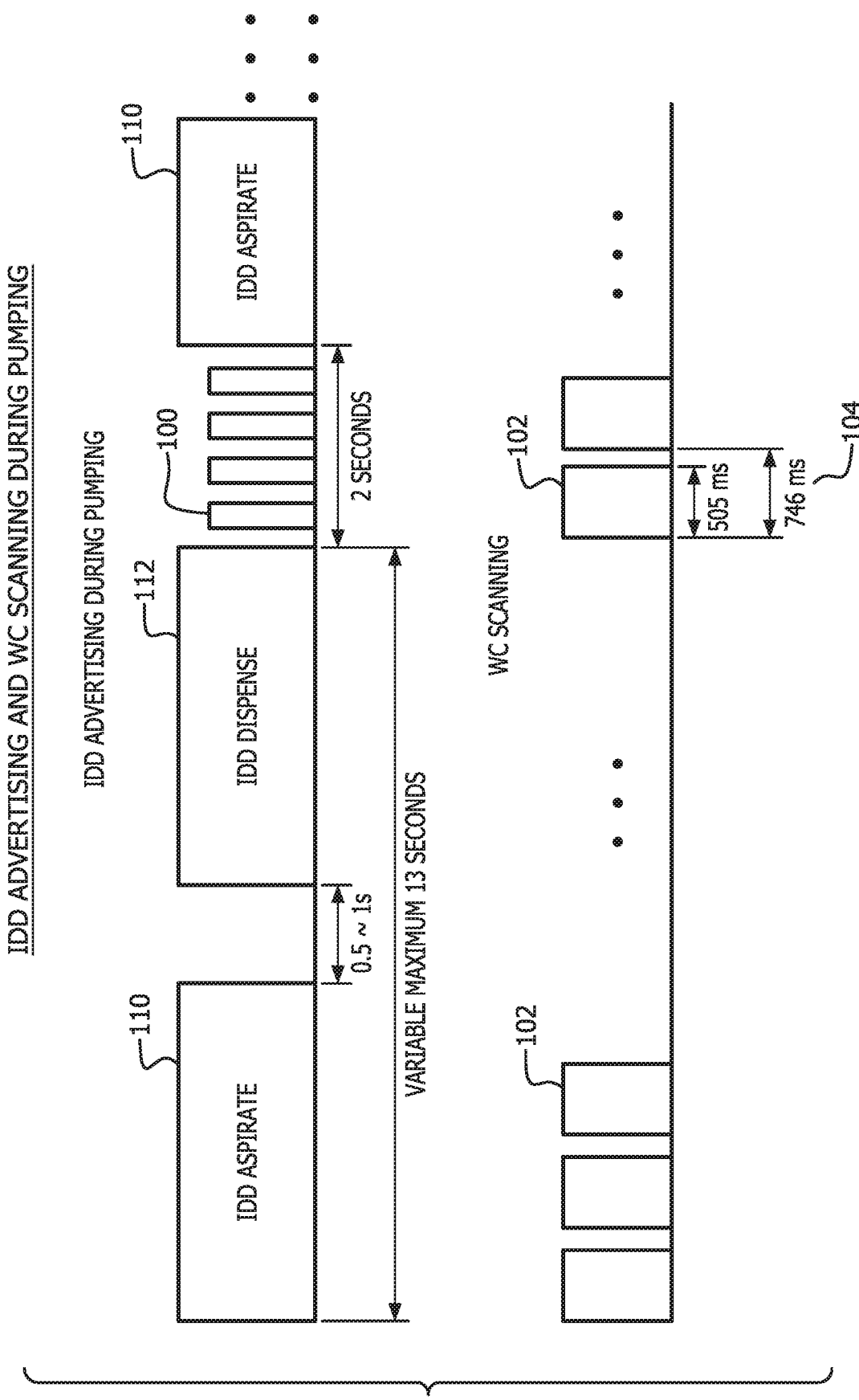

An illustrative example of a specific intradevice pairing protocol for pairing the IDD 12 with the WC 14 will now be described with reference to FIGS. 3, 4 and 5. In accordance with an illustrative embodiment and as described below, the intradevice pairing protocol has particular advertising and scanning window durations, and corresponding intradevice pairing software is provided to the IDD 12 and WC 14 for a secure, bonded relationship. It is to be understood that the timing described with reference to FIGS. 3, 4 and 5 is for illustrative purposes and that timing specifications can be different depending on the design and inputs used for a particular device pairing application. As will also be discussed below, an interdevice, legacy Classic Bluetooth® pairing protocol available to, and commonly used among, various devices 16 can be also used instead for communications requiring less security than, for example, control communications for a delivery device and therefore no bonded relationship as between the IDD 12 and WC 14.

Example IDD 12 advertising and WC 14 scanning before intradevice pairing are illustrated FIG. 3. Upon waking up and before pairing, every 250 ms (+/−10%) as indicated at 106, the IDD 12 advertises with IDD Startup Advertising Data packets 100, and waits for 3 ms (+/−10%) for the possible reply from a WC 14. At the WCMP 30's request, the WCCP 32 initiates the communication by starting scanning the IDD advertisement every 746 ms (+/−10%) 104 for about a 505 ms (+/−10%) scanning window 102. At the end of the scanning time period 104, if the WCCP 32 does not detect any advertising packet 100 within a transport layer timeout period, the WCCP stops scanning and sends a Nack response with a Transmission Timeout error code. The WCCP 32 goes to sleep if no advertising is detected.

The WC 14 can determine if a particular type of device 12 is in its vicinity. For example, the IDD 12 Startup Advertising Data can comprise IDD identifying information (e.g., selected dynamic and/or static parameters or values that identify a type of device such as manufacturer and/or model or other characteristic) such that the WC 14 can be configured to only pair with devices or IDDs having designated IDD identifying information and not with other devices that do have the designated IDD identifying information. Thus, if the WCCP 32 determines that the IDD 12 Startup Advertising Data has IDD identifying information relating, for example, to its particular manufacturer, the WC 14 can pair with the advertising IDD 12. If not, the WCCP 32 continues scanning.

Example IDD 12 advertising and WC 14 scanning after pairing are illustrated FIG. 4. After intradevice pairing, and optionally when the IDD 12 is not actively pumping, the IDD advertises with a IDD Periodic Data Packet 100 at a selected interval 108 (e.g., every 1 second (±/−10%)). The IDD Periodic Data Packet can be provided with an alert code or other data indicating a condition requiring generation of a notification to the user(s) or otherwise indicating a request for notification. After each advertisement 100, the IDD 12 waits for 30 ms (+/−10%) for the possible reply from the WC 14. After pairing, at the WCMP 30's request, the WCCP 32 initiates the communication by starting scanning the IDD advertisement every 746 ms (+/−10%) 104 for a 505 ms (+/−10%) scanning window 102.

Example IDD 12 advertising and WC 14 scanning during pumping are illustrated in FIG. 5. If the IDD 12 is delivering a medication such as insulin, it can optionally advertise every 500 ms for 2 seconds at the end of a dispense stroke 112. Even though it is not indicated in FIG. 6, during the break time between IDD aspirate periods 110 and dispense periods 112, the IDD 12 still tries advertising if possible. When the IDD 12 is pumping, at the WCMP 30's request, the WCCP 32 initiates the communication by starting scanning the IDD advertisement every 746 ms (+/−10%) 104 for 505 ms (+/−10%) scanning windows 102.

In the illustrated example of FIGS. 3, 4 and 5, the intradevice wireless protocol implemented by the WC 14 and its paired IDD 12 configures the IDD 12 to only accept a control command from the paired WC 14 such as a wireless command to deliver insulin or to configure dosage amounts and to only send sensitive device data or information (e.g., delivered drug amounts) to the paired WC 14. This bonded, specific intradevice communication relationship between the WC 12 and IDD 14 ensures that no other device can control operation of the IDD 12 for safety and security reasons or receive sensitive data or information, and this bonded, specific intradevice communication relationship remains until the IDD is deactivated. After IDD deactivation, the WC 14 is free to pair with a new IDD 12; however, at any given time, the WC 14 is preferably only allowed to pair with one IDD 12. If the WC 14 is a smartphone, as opposed to a dedicated wireless controller, then the smartphone can be configured with a medical device control app 14 that controls the smartphone's pairing and resulting bonded relationship with only one IDD 12 at a time.

It is to be understood, however, that a standard or legacy Classic Bluetooth® protocol can be used by the IDD 12 to pair with the WC or smartphone 14 and optionally pair with another device 16 (e.g., a smart watch or Bluetooth®-enabled headset or earpiece), or can be used by the WC 14 to pair with another device 16, to merely exchange medical device data that does not require the same bonding relationship limitation of intradevice pairing protocol described above in connection with FIGS. 3, 4 and 5. For example, if the IDD 12 is merely using the Bluetooth® link to request that a notification be generated at the WC 14 or other device 16, and therefore the IDD 12 is not sending sensitive IDD operational status data or receiving commands, then a common interdevice protocol (e.g., legacy Classic Bluetooth®) can be used for pairing with and requesting notification by another device 14,16 that also supports the same protocol. To send less sensitive information, such legacy Classic Bluetooth®-enabled connectivity need not limit the device(s) 16 to which the IDD 12 is paired, or require specific, non-standard intervals and therefore does not require software in the IDD 12 and the WC 14 and/or other device 16 that supports a specific intradevice protocol for wireless connectivity having a level of security needed for safe medical device operation. In other words, the IDD 12 and the WC 14 can employ a secure, intradevice BLE-based communication protocol for secure drug delivery control operations, and a common interdevice and standard Bluetooth® protocol (e.g., legacy Classic Bluetooth) can be used for pairing the IDD 12 with devices 14 and/or devices 16 (e.g., Bluetooth® earpieces or smart watches) that are merely receiving requests for notifications about IDD operational problems, or collecting status or log data from the IDD 12.

The medical device 12, dedicated controller 14 and smartphone with medical device controller app 14 are configured to each implement at least two different wireless communication protocols for exchanging, respectively, data or signals characterized as having at least two different levels of security requirements. For example, with reference to FIGS. 2A, 2B and 2C, the RF components 54 in the medical device 12, the RF components 38 in the dedicated controller 14 or similar RF components in the smartphone can comprise antenna(s) and matching circuit(s) as needed to accommodate at least the two different wireless communication protocols. For example, the wearable medical device 12 is configured with a BT stack that allows the device 12 to pair with its controller 14 in a secure bonded relationship, but to send signals requiring less security (e.g., requests for generation of notifications) to other devices (e.g., a BT-enabled headset or smart watch) 16 using a more ubiquitous standard BT protocol with broadcast mode. The medical device 12, controller 14 or medical device control app 14 for a smartphone are programmed or otherwise configured to determine when to use the two different wireless communication protocols, depending on the type of operation and/or the type of information to be exchanged. For example, the medical device 12 and controller or control app 14 are programmed or otherwise configured to constrain medical device configuration and control operations and related data and signals (e.g., set dose amounts, commands to initiate and terminate delivery operation, delivered drug amounts) to communication via the more secure of the two different wireless communication protocols (e.g., a specific intradevice protocol). For example, the data related to configuration and control operations that require more secure communication can be provided with metadata or stored in a designated memory location that signifies that the more secure of the two communication protocols is needed to exchange it between the medical device 12 and the controller or control app 14 and to preclude its communication to a device 16 that does not also employ the same secure wireless protocol such as the specific intradevice protocol. Similarly, device 12 requests for generation of notifications, or log or history data, that are designated to be less sensitive than device 12 configuration and control data can be provided with metadata or stored in a designated memory location that signifies that the less secure of the two communication protocols can be used to communicate the requests for generation of notifications or transmit the log data from the medical device 12 to the controller or control app 14 and/or device(s) 16 and/or from the controller or control app 14 to the device(s) 16.

As stated above, the LED 62 can be used for notification. For example, the LED 62 can blink at critical notification(s) of the IDD 12. Critical notifications can include, but are not limited to, memory corruption in the IDD 12, a reservoir empty or near empty condition, a pump malfunction such as the IDD 12 pumping mechanism 52 not running during an intended insulin delivery, low IDD battery, or other condition that leads to the IDD's end of life, etc. Wearable medical devices such as a patch pump 12 are often worn under a patient's clothing. Accordingly, if a wearable medical device has an indicator (e.g., an LED 62), a patient's view of the indicator is often obscured by the patient's clothing. In addition, even if the visual indicator 62 is not obscured by clothing, LED notifications on a wearable medical device 12 may not be perceived by a vision impaired patient, or elderly or mentally impaired patient. Accordingly, a tactile and/or auditory indicator 62 can be helpful to these types of patients, particularly tactile indicators for deaf or hearing impaired patients.

With reference to FIGS. 6A through 10, apparatuses and methods are provided in accordance with three illustrative embodiments for informing a patient wearing a medical device when a critical notification occurs. As described below, the medical device 12 (e.g., an IDD) can be configured to: (1) generate a request for an audio signal to be generated at the WC 14 or another device 16 such as smartphone or BT-enabled headset using a BLE communication from the IDD 12; and/or (2) generate a request for a vibration notification to be generated at the WC 14 or another device 16 such as a smartphone, swart watch or BT-enabled wristband (e.g., fitness monitor) using BLE communication from the IDD 12; and/or (3) transmit a BLE signal from the IDD 12 to the WC 12 or another device 16 such as a smartphone, swart watch to request that the device 14 or 16 send a message(s) to another person (e.g., a caregiver) via the other person's smartphone, for example. One or a combination of these three notification methods can be implemented using the BT stacks of the IDD 12 and WC 14 described above. Further, if the IDD 12's request for notification generation is fulfilled by the WC 14 or a smartphone 14 configured to control IDD operation, the request can be sent using either one of the intradevice or interdevice BT protocols described above. If the IDD 12's request for notification generation is fulfilled by a device 16 that is not configured to control IDD operation, the request can be sent using a wireless communication protocol compatible with the device 16 and that may have less security associated with it such as the interdevice BT protocol described above.

The illustrative embodiments realize a number of advantages over existing wearable medical devices including, but not limited to, ensuring patients of different sensory and cognitive abilities are able to receive notifications regarding their medical device 12, particularly notifications regarding critical conditions occurring in their devices 12. Patients, for example, can hear an audio signal requested by their medical device 12 (e.g., IDD) and generated by a BT-enabled headset 16 or smartphone 14,16 or WC 14. Patients can feel a vibration requested by their medical device 12 and generated by their BT-enabled wristband 16 or at their smart phone 14,16 or WC 14, A patient's caregiver can receive a message generated at their device (e.g., a smartphone) in response to a request for generation of message by the IDD 12. It would be great to take proper action at right time. In any event, the illustrative embodiments facilitate a patient or caregiver being able to take proper action regarding the patient's medical device 12 condition (e.g., replace the IDD 12, reset or power it one, replace battery, etc.) upon a timely notification. Further, by having the medical device 12 merely generate a request for a notification that is fulfilled at different device 14 or 16, there is no need to change the existing medical device 12 hardware or increase medical device 12 complexity or cost because the request for notification can be generated and transmitted from the medical device 12 using a wireless communication interface already existing in the medical device 12. In addition, a patient can use the enhanced notifications provided by the illustrative embodiments without hesitation in public areas because the requested notification can be a discreet vibratory notification from a smartphone or smart wristband, or an audible signal in a BT-enabled headset, for example. Security of the medical device 12 (e.g., IDD) and the controller 14 (e.g., WC) control operations is maintained because the enhanced notifications provided by the illustrative embodiments limit operations with a third device 16 to notifications only and not medical device 12 control.

Figure 6A:
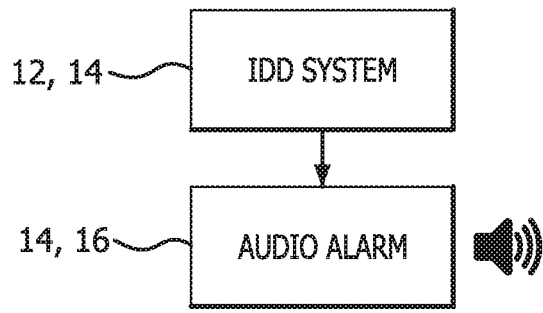
FIGS. 6A, 6B and 6C illustrate a first use case of a medical device requesting an audible notification generated at another device in accordance with an illustrative embodiment.
Figure 6B:
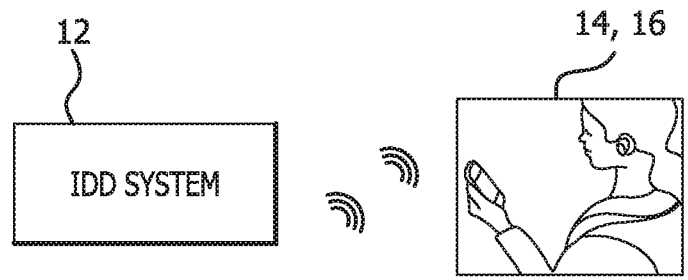
Figure 6C:
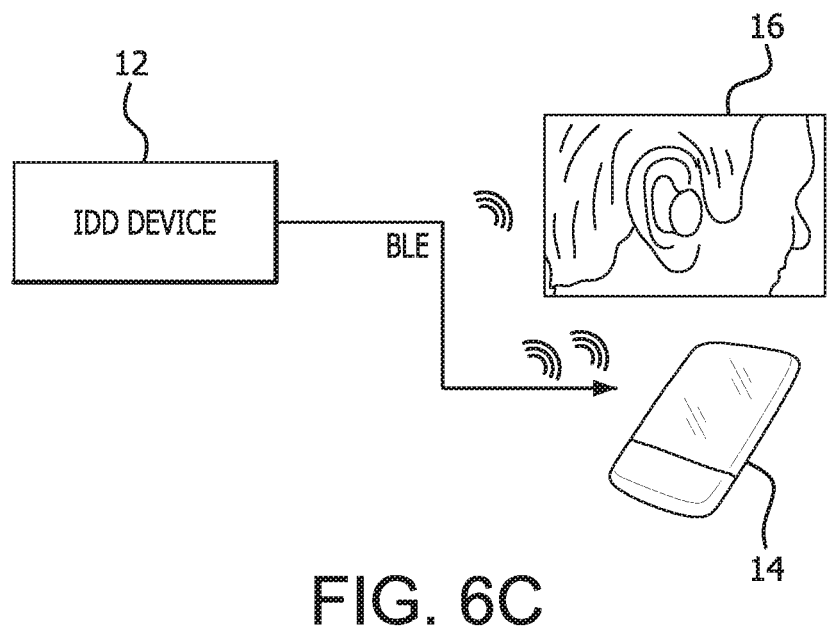

FIG. 6A depicts generally an example medical device 12 (e.g., IDD) that generates a request for an audible notification. With reference to FIG. 6B, the request for an audible notification can be transmitted wirelessly by the IDD 12 to a dedicated WC 14, or directly to a smartphone 14 operating as the IDD controller, wherein the WC or smartphone 14 is configured to generate an audible notification via its speaker and/or buzzer or other sound generating device. As stated above, the wireless protocol for transmitting the request for notification from the IDD 12 to the controller 14 can be either the intradevice protocol or an interdevice protocol. FIG. 6C depicts an illustrative embodiment wherein a patient does not have a smartphone but rather uses a dedicated wireless controller 14 with the IDD 12. As shown in FIG. 6C, the IDD 12 can transmit a request for notification to the WC 14 (e.g., using either the intradevice protocol or a interdevice protocol). The WC 14, in turn, is configured to transmit an audible signal to a device 16 such as a BT-enabled headset for playback to its user (e.g., a diabetic patient using a BT-enabled device for audio signals).

Figure 7A:
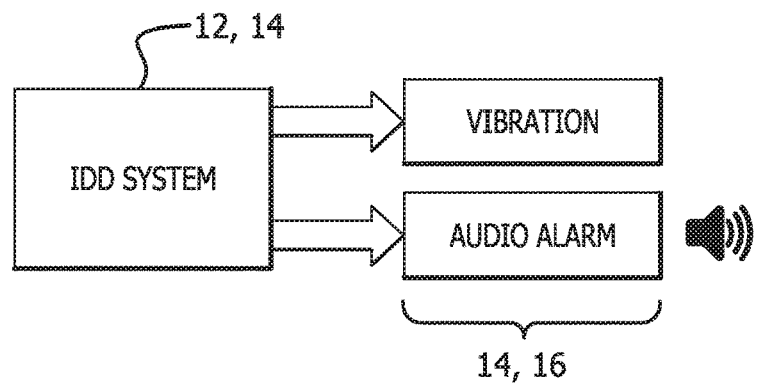
FIGS. 7A, 7B and 7C illustrate a second use case of a medical device requesting a vibratory notification generated at another device in accordance with an illustrative embodiment.
Figure 7B:
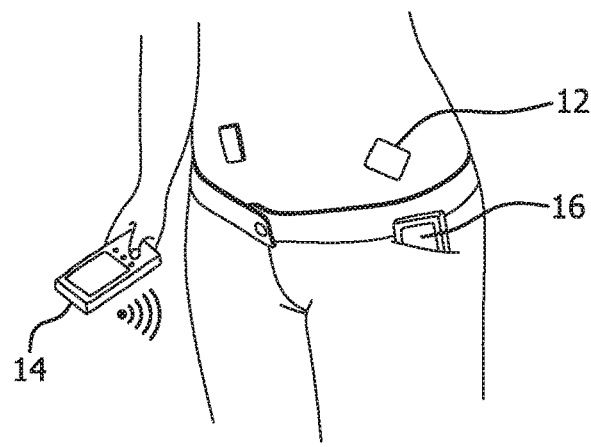
Figure 7C:
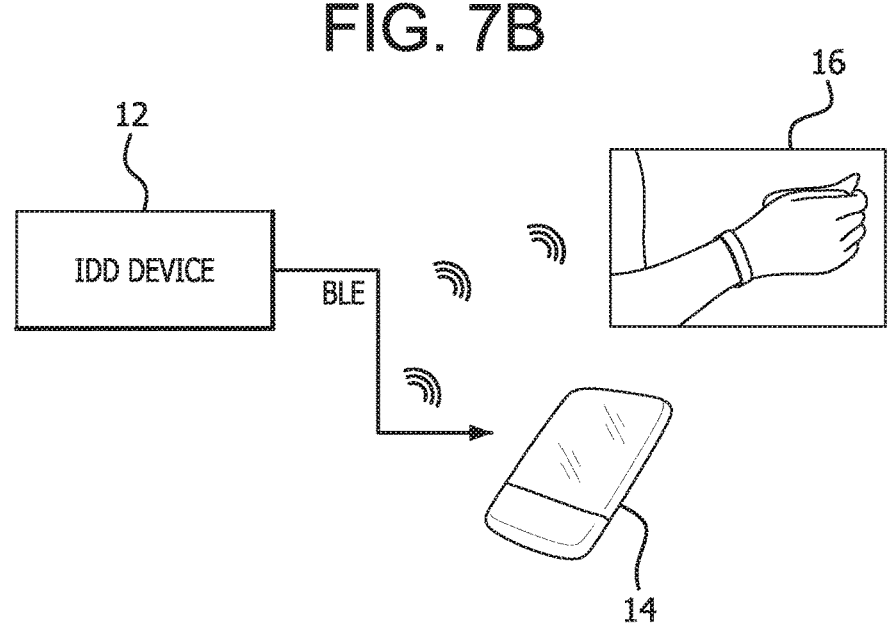

FIG. 7A depicts generally an example medical device 12 (e.g., IDD) that generates a request for a vibratory or tactile notification. With reference to FIG. 7B, the request for a vibratory or tactile notification can be transmitted wirelessly by the IDD 12 to a dedicated WC 14, or directly to a smartphone 14 operating as the IDD controller, wherein the WC or smartphone 14 is configured to generate a vibratory or tactile notification via its vibratory device or other tactile indicator. Alternatively, the reusable, dedicated WC 14 can be configured without a tactile indicator to minimize its complexity and cost, in which case the WC 14 or IDD 12 is configured to send a request for tactile notification to a device 16 comprising a tactile indicator. As stated above, the wireless protocol for transmitting the request for notification from the IDD 12 to the controller 14 can be either the intradevice protocol or an interdevice protocol. To maintain security of IDD control operations, the wireless protocol for transmitting the request for notification from the IDD 12 or the controller 14 to a device 16 is via an interdevice protocol that is not configured to send or receive IDD control commands or sensitive device data. FIG. 7C depicts an illustrative embodiment wherein a patient does not have a smartphone but rather uses a dedicated wireless controller 14 with the IDD 12. As shown in FIG. 7C, the IDD 12 can transmit a request for notification to the WC 14 (e.g., using either the intradevice protocol or a interdevice protocol). The WC 14, in turn, is configured to transmit a request for generation of a vibratory or other tactile indication to a device 16 such as a smart watch or other smart wristband device that is BT-enabled or configured to communicate with the WC 14 via near field communication (NFC) or other wireless protocol, which can be an interdevice protocol that is not configured to send or receive IDD control commands or sensitive data. For example, the patient can use a wristband or wearable patch device 16 comprising a BLE interface, vibration motor and battery. Operating vibration motor or other tactile indicator electronic circuit in a remote device 16 to indicate a notification helps hearing impaired patients, caregivers, and patients who wear the IDD 12 in loud environments such as a place of employment characterized by noise from industrial plant operations or other sources (motors of equipment or airplanes) to be ensured access to notifications to timely address a critical condition detected or occurring at the IDD 12.

Figure 8A:
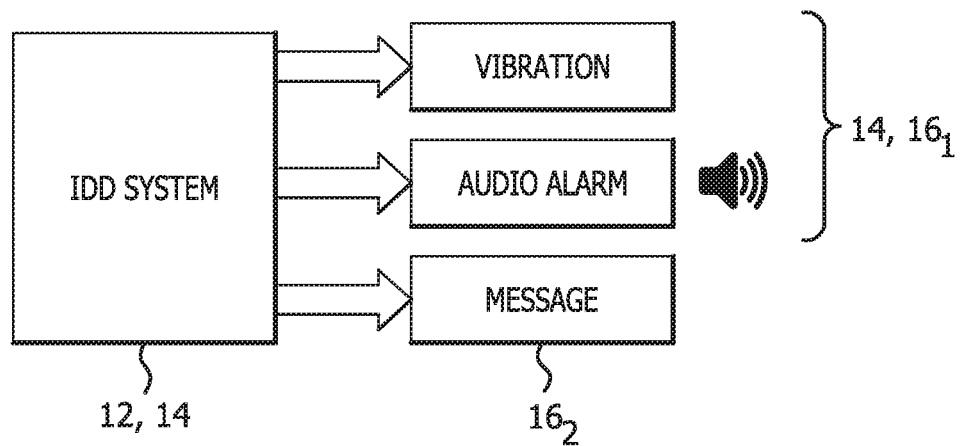
FIGS. 8A and 8B illustrate a third use case of a medical device requesting an audible and/or vibratory notification generated at another device, and transmission of a message to yet another device via cellular communication, in accordance with an illustrative embodiment.
Figure 8B:
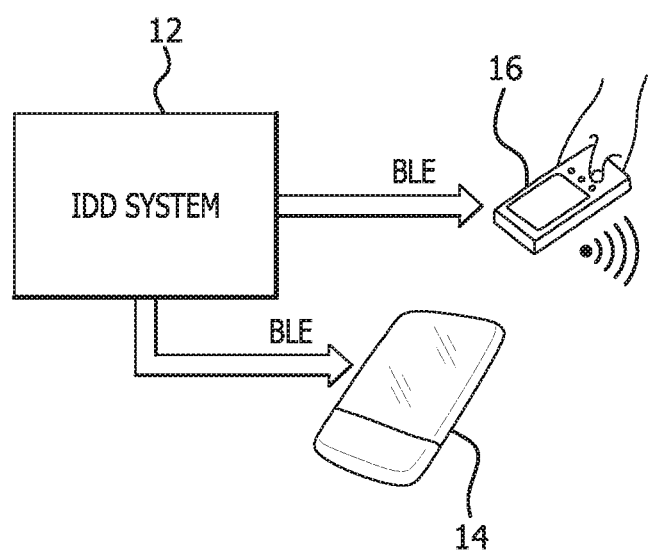

FIG. 8A depicts generally an example medical device 12 (e.g., IDD) that (1) generates a request for an audible and/or tactile notification and transmits it to a controller 14 or other device that fulfills the request by outputting the requested notification(s) to the patient as described above in connection with FIGS. 6A through 7C, and also (2) generates a request that a message be transmitted to a caregiver regarding the IDD critical condition. For example, the IDD 12 can pair with a WC 14 or smart watch or smartphone 16$_1$ that stores a caregiver cell number(s). The IDD 12 and WC 14 can use, for example, BLE to communicate the request for notification from the IDD 12 to the WC 14 or smartphone 14 operating as an IDD controller. The WC or other IDD controller 14 in turn can use cellular communication to complete a call to a device 16$_2$ used by the family member(s) or physician or school nurse or other caregiver. The device 16$_2$ in turn receives the message or request for a notification and generates the notification, as illustrated in FIGS. 8A and 8B. This illustrative embodiment is advantageous because the message to the caregiver(s) is sent through a smartphone interface with wireless controller 14 using BLE or other interdevice protocol that need not be configured to send and receive IDD control commands. The IDD and WC do not require additional hardware for this function, thereby avoiding increased complexity and cost.

In addition, the IDD 12 and/or WC or other IDD controller 14 can be configured to allow the patient to select among different modes of enhanced, remote notifications such as vibration or tactile notification and/or audible notification, depending on the controller 14 and the devices 16 paired with the controller 14 and/or IDD 12. For example, the controller 14 can be programmed to generate display screens during a set-up mode with user prompts that allow the IDD user 12 to indicate criteria such as paired device selection (e.g., indicating selected the device(s) 16 to which it is paired) and corresponding notification mode (e.g., audible mode and/or tactile mode to be employed by that paired device for the notification). For example, any of the medical device 12, controller 14 or other device 16 can be configured to generate user prompts that allow a user, depending on the notification circuity and functionality at the controller 14 (i.e., WC or smartphone) and the paired devices (16), to select preferred type(s) of notifications to be generated at the controller 14 and/or device(s) 16.

FIG. 9 is a flow chart depicting operations of an example medical device 12 (e.g., IDD 12) to request a notification generated at another device 14, 16 in accordance with illustrative embodiments. The IDD 12 can be programmed or otherwise configured to perform the operations, for example, and the operations may incorporate all or only a subset of the steps depicted in FIG. 9. The IDD 12 is paired with a dedicated WC 14 or smartphone 14 configured to control the IDD 12 (block 120). The IDD 12 is configured to monitor for conditions occurring within the IDD that require the user to be notified such as the afore-mentioned critical conditions, for example (block 122). If a condition is detected requiring user notification (block 124), the IDD 12 is configured to generate a request for notification (blocks 128 and 130) for transmission to the controller 14 (block 132) and/or another device 16 (block 124). As stated above, if the WC 14 has the requisite indicator for the desired notification mode (e.g., auditory or tactile), the IDD 12 can transmit the request for notification using the secure BLE intradevice protocol. Alternatively, the IDD 12 can send the request for notification directly to a device 16 or via the controller 14 via a less secure BT interdevice protocol, for example. Upon receiving a notification (e.g., via the LED 62, or via an enhanced notification generated at a device 14, 16 remote from the IDD 12, the IDD user or a caregiver can attempt to resolve the issue with the IDD that resulted in detection of a condition warranting notifying the user (block 134). If the condition cannot be resolved, then the IDD 12 can be disabled manually by the user or caregiver, or automatically via its processor 60.

Figure 10:
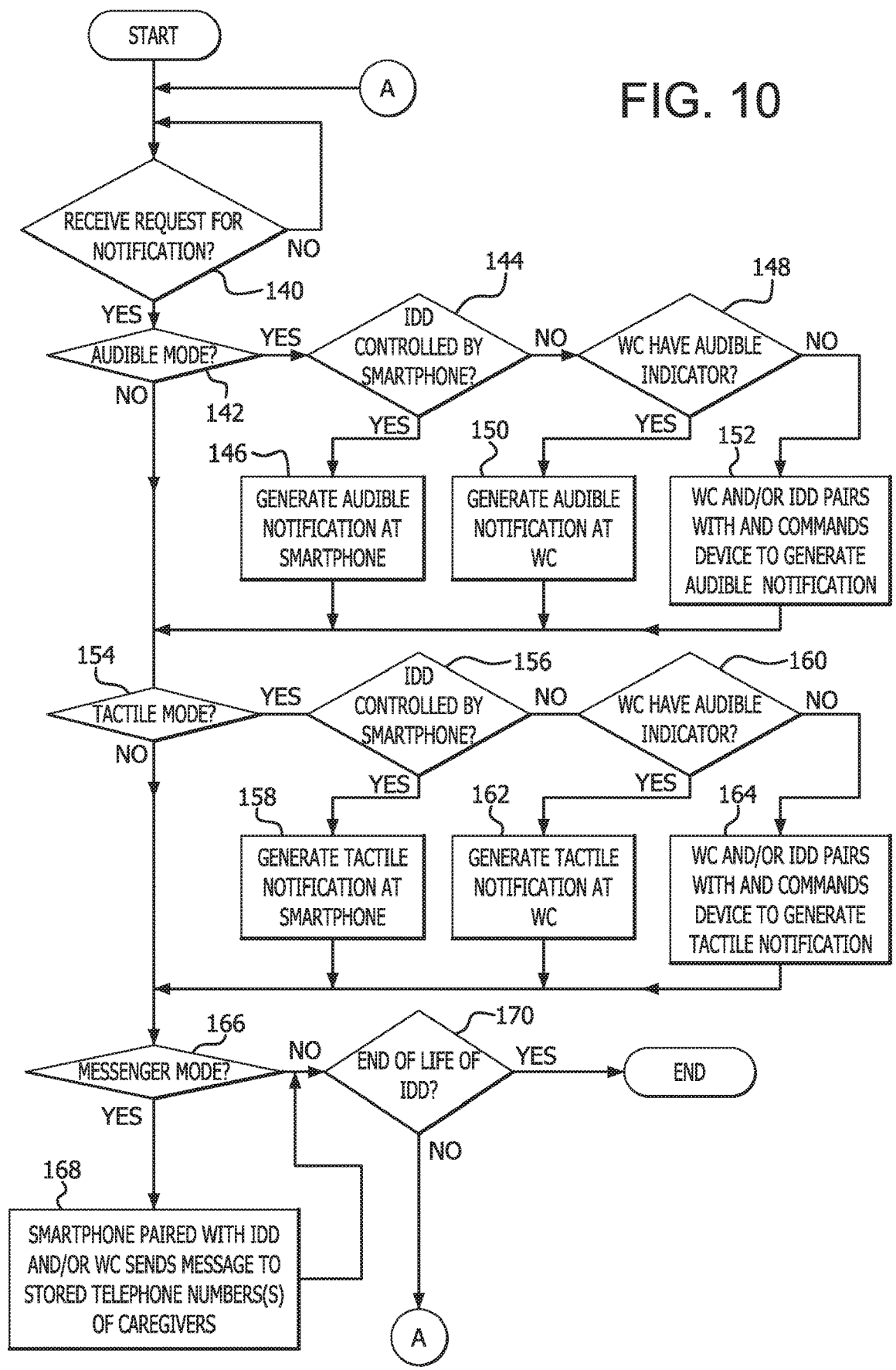
FIG. 10 is a flow chart depicting operations of at least one other device to generate the requested notification(s) in accordance with an illustrative embodiment.

FIG. 10 is a flow chart depicting operations of at least one other device 14, 16 to generate the notification(s) requested by a wearable medical device (e.g., IDD 12) in accordance with illustrative embodiments. With reference to block 140, the device 14, 16 is programmed or otherwise configured determine if a request for notification has been received (e.g., directly from the IDD 12 or from the WC 14 or smartphone 14 being used to control the IDD 12). As stated above, the IDD can request remote generation of notifications at a device 14 and/or 16 using one or more modes such as an auditory mode (block 142), a tactile mode (154) and a messenger mode (block 166), For example, it is to be understood that the device 14,16 only operates in an auditory mode or a tactile mode for notification, or in different combinations of subsets of all of the modes, or in any of all of the available modes, depending on how the IDD 12, WC 14 and/or device 16 are configured.

With reference to blocks 144 and 156 in FIG. 10, if the medical device 12 (e.g., IDD) is controlled by a smartphone 14 (e.g., as opposed to a dedicated WC without cellular operation or limited indicators such as only an LCD display), the smartphone 14 can fulfill the IDD 12's request for notification by generating, respectively, an audible notification (block 146) and/or tactile notification (block 158). On the other hand, with reference to blocks 148 and 160 in FIG. 10, if the IDD 12 is controlled by a dedicated WC 14, for example, the WC 14 can fulfill the IDD 12's request for notification by generating, respectively, an audible notification (block 150) and/or tactile notification (block 162), depending on its hardware and software configuration for generating indications. Alternatively, with reference to blocks 152 and 164 in FIG. 10, the IDD 12 or WC 14 can pair with another device 16 using, for example, an interdevice wireless protocol and request generation of a notification at that device 16. For example, the IDD 12 or WC 14 can command a BT-enabled headset to generate an audible notification (block 152). The IDD 12 or WC 14 can command a BT-enabled smart watch or other BT-wristband to generate a tactile notification (block 164). Thus, the device 14, 16 (e.g., a smartphone, WC. BT-headset, smart watch, BT-enabled wristband, or other device 16 with an indicator) can receive a request for notification from the IDD 12 directly or from an IDD controller 14 and generate the requested notification using its indicator hardware and/or software, depending on how the IDD 12 and/or controller 14 are configured to generate notifications or indications.

With reference to block 166 in FIG. 10, the WC or smartphone 14 controlling the IDD 12 can store number(s) of caregiver(s) and, operating in the messenger mode, send notification (e.g., via cellular communication) to the caregiver(s) in response to receiving a request for notification from the IDD 12. If the IDD 12 and/or WC 14 indicates an end of life status for the IDD 12, the request fulfillment process illustrated in FIG. 10 can be terminated or suspended until the WC 14 and/or the device 16 pairs with a new IDD 12, for example.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the illustrative embodiments can be easily construed as within the scope of the invention by programmers skilled in the art to which the illustrative embodiments pertain. Method steps associated with the illustrative embodiments can be performed by one or more programmable processors executing a computer program, code or instructions to perform functions (e.g., by operating on input data and/or generating an output). Method steps can also be performed by, and apparatus of the illustrative embodiments can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The above-presented description and figures are intended by way of example only and are not intended to be limiting in any way except as set forth in the following claims. It is particularly noted that persons skilled in the art can readily combine the various technical aspects of the various elements of the various illustrative embodiments that have been described above in numerous other ways.

The invention claimed is:

1. A medical device for a user, comprising:
a radio frequency (RF) circuit configured to exchange RF signals with a second device in a body area network (BAN) of the user in which the medical device and the second device operate for the user and the medical device is chosen from a fluid delivery device, a glucose meter, and a health monitor;
a memory device; and
a processing device connected to the RF circuit and the memory device, and configured to detect at least one designated notification condition in the medical device, generate a request for notification in response to detection of at least one designated notification condition, and transmit via the RF circuit the request wirelessly to the second device to prompt the second device to actuate an indicator that is remote from the medical device and generate an indication to the user chosen from an audible indication and a tactile indication;
wherein the second device is at least one device chosen from a controller and a smartphone and is paired wirelessly with the medical device, the second device having at least one indicator chosen from an audible indicator and a tactile indicator;
wherein the second device is paired with a third device, the third device comprising at least one indicator chosen from an audible indicator and a tactile indicator, and the medical device being connected to the third devices by at least one of directly connected or indirectly connected via the second device; and
wherein the processing device and RF circuit are configured to employ a selected one of at least two wireless communication protocols to exchange, via the RF circuit, RF signals with at least one device chosen from the second device and the third device, wherein the at least two wireless communication protocols comprises a first communication protocol that is employed by the processing device to pair the second device with the medical device to securely send secure information chosen from configuration data, medical device operation data, and control signals to operate the medical device, and a second communication protocol that is employed by the processing device to pair with at least one of the second device and the third device to send information chosen from medical device status data and notifications that requires less wireless security than the secure information.

2. The medical device of claim 1, wherein the medical device is a wearable device.

3. The medical device of claim 1, wherein the third device is selected from the group consisting of a smart watch, a Bluetooth®-enabled headset, a portable monitoring device, and a Bluetooth®-enabled wristband device.

4. A medical device, comprising:
a radio frequency (RF) circuit configured to exchange RF signals with a second device;
a memory device; and
a processing device connected to the RF circuit and the memory device, and configured to detect at least one designated notification condition in the medical device, generate a request for notification in response to detection of at least one designated notification condition, and transmit via the RF circuit the request wirelessly to the second device to prompt the second device to actuate an indicator that is remote from the medical device;
wherein the processing device and RF circuit are configured to employ a selected one of at least two wireless communication protocols to exchange, via the RF circuit, RF signals with at least one device chosen from the second device and an third device, wherein the at least two wireless communication protocols comprises a first communication protocol that is employed by the processing device to pair the second device with the medical device to securely send secure information chosen from configuration data, medical device operation data, and control signals to operate the medical device, and a second communication protocol that is employed by the processing device to pair with at least one of the second device and the third device to send information chosen from medical device status data and notifications that requires less wireless security than the secure information.

5. The medical device of claim 1, further comprising a user interface, wherein the processing device is configured to operate the user interface to generate user selection prompts that guide a user to configure notification preferences based on criteria chosen from paired device selection and corresponding notification mode, wherein the paired device selection prompts a user to indicate at least one device paired with the medical device, and wherein the notification mode prompts the user to select a mode chosen from an audible mode and a tactile mode to be employed by that paired device for the notification.

6. A device for generating a notification from a medical device, comprising
  at least one indicator;
  a radio frequency (RF) circuit configured to exchange RF signals with the medical device in a body area network (BAN) of the user in which the medical device and the second device operate for the user;
  a memory device; and
  a processing device connected to the at least one indicator, the RF circuit and the memory device, and configured to wirelessly receive via the RF circuit a request for notification from the medical device, the medical device generating the request for notification in response to detection of at least one designated notification condition, and to perform a notification operation chosen from generating an audible signal via the at least one indicator, wirelessly transmitting via the RF circuit a request to a third device to generate an audible signal, generating a vibratory notification signal via the at least one indicator, and wirelessly transmitting via the RF circuit a request to the third device to generate a vibratory notification signal;
  wherein the processing device and RF circuit are configured to employ a selected one of at least two wireless communication protocols to exchange, via the RF circuit, RF signals with at least one device chosen from the medical device and the third device, wherein the at least two wireless communication protocols comprises a first communication protocol that is employed by the processing device to pair the device with the medical device to securely receive secure information chosen from configuration data, medical device operation data, and control signals to operate the medical device, and a second communication protocol that is employed by the processing device to pair with at least one of the medical device and the third device to receive from the medical device less secure information chosen from medical device status data and notifications that requires less wireless security than the secure information and to send the less secure information to the third device.

7. The device of claim 6, wherein the device is at least one device chosen from a controller and a smartphone and is paired wirelessly with the medical device, and the third device is selected from the group consisting of a smart watch, a Bluetooth®-enabled headset, a portable monitoring device, and a Bluetooth®-enabled wristband device.

8. The device of claim 6, further comprising a user interface, wherein the processing device is configured to operate the user interface to generate user selection prompts that guide a user to configure notification preferences based on criteria chosen from paired device selection and corresponding notification mode, wherein the paired device selection prompts a user to indicate at least one device paired with the medical device, wherein the notification mode prompts the user to select a mode chosen from an audible mode and a tactile mode to be employed by that paired device for the notification, and wherein the paired device is chosen from the device, the third device and a fourth device.

9. A method of generating a notification from a medical device comprising:
  configuring the medical device of a patient to detect at least one designated notification condition;
  configuring the medical device to generate a request for notification in response to detection of at least one designated notification condition, the notification being an indication to the patient chosen from an audible indication and a tactile indication;
  transmitting the request wirelessly to a second device comprising an indicator that is located in a body area network (BAN) of the patient in which the medical device and the second device operate for the patient and configured to actuate the indicator in response to the request to generate the indication; and
  employing a selected one of at least two wireless communication protocols for exchange of radio frequency signals with at least one other device chosen from the second device and a third device, the at least two wireless communication protocols comprising a first communication protocol that is employed by the medical device to pair the second device with the medical device to securely send secure information chosen from configuration data, medical device operation data, and control signals to operate the medical device, and a second communication protocol that is employed by the medical device to pair with at least one of the second device and the third device to send information chosen from medical device status data and notifications that requires less wireless security than the secure information.

10. The method of claim 9, wherein the indicator is an audio output device configured to output an audible output signal as the audible indication.

11. The method of claim 9, wherein the second device is selected from the group consisting of a cell phone, a Bluetooth-enabled ear piece, a smart watch, a portable communication device, a portable computing device, a portable wireless controller configured to control the medical device.

12. The method of claim 9, wherein the notification condition is selected from the group consisting of an end of life state of the medical device, a corrupted memory in the medical device, near empty reservoir in the medical device, empty reservoir in the medical device, and low battery in the medical device.

13. The method of claim 9, further comprising generating user selection prompts that guide a user to configure notification preferences based on criteria chosen from paired device selection and corresponding notification mode, wherein the paired device selection prompts a user to indicate at least one device paired with the medical device, and wherein the notification mode prompts the user to select a mode chosen from an audible mode and a tactile mode to be employed by that paired device for the notification.

14. A method of generating a notification from a medical device comprising:

wirelessly receiving a request for notification from the medical device at a second device located in a body area network (BAN) of a user in which the medical device and the second device operate for the user, the medical device being configured to generate the request for notification in response to detection of at least one designated notification condition;

operating the second device to perform a notification operation, the notification operation chosen from generating an audible signal via at least one indicator, wirelessly transmitting a request to a third device to generate an audible signal, generating a vibratory notification signal via at least one indicator, and wirelessly transmitting a request to the third device to generate a vibratory notification signal; and employing a selected one of at least two wireless communication protocols for exchange of radio frequency signals with at least one other device chosen from the medical device and a third device, the at least two wireless communication protocols comprising a first communication protocol that is employed by the processing device to pair the device with the medical device to securely receive secure information chosen from configuration data, medical device operation data, and control signals to operate the medical device, and a second communication protocol that is employed by the device to pair with at least one of the medical device and the third device to receive from the medical device less secure information chosen from medical device status data and notifications that requires less wireless security than the secure information and to send the less secure information to the third device.

15. The method of claim 14, further comprising the third device actuating an indicator in response to receiving the request transmitted from the second device.

16. The method of claim 14, further comprising generating, via a device chosen from the medical device, the second device and the third device, user selection prompts that guide a user to configure notification preferences based on criteria chosen from paired device selection and corresponding notification mode, wherein the paired device selection prompts a user to indicate at least one device paired with the medical device, wherein the notification mode prompts the user to select a mode chosen from an audible mode and a tactile mode to be employed by that paired device for the notification, and wherein the paired device is chosen from the second device, the third device and a fourth device.

* * * * *